US012773153B2

(12) United States Patent
Cobos Gil

(10) Patent No.: US 12,773,153 B2
(45) Date of Patent: Oct. 27, 2026

(54) METHOD FOR OBTAINING AN ELECTROCARDIOGRAM IN PRONATED SUBJECTS

(71) Applicant: FUNDACIÓN PARA LA INVESTIGACIÓN BIOMÉDICA DEL HOSPITAL CLÍNICO SAN CARLOS, Madrid (ES)

(72) Inventor: Miguel Angel Cobos Gil, Madrid (ES)

(73) Assignee: FUNDACIÓN PARA LA INVESTIGACIÓN BIOMÉDICA DEL HOSPITAL CLÍNICO SAN CARLOS, Madrid (ES)

( * ) Notice: Subject to any disclaimer, the term of this patent is extended or adjusted under 35 U.S.C. 154(b) by 134 days.

(21) Appl. No.: 18/955,183

(22) Filed: Nov. 21, 2024

(65) Prior Publication Data

US 2025/0169738 A1 May 29, 2025

(30) Foreign Application Priority Data

Nov. 29, 2023 (EP) .................................... 23383226

(51) Int. Cl.
*A61B 5/318* (2021.01)
*A61B 5/346* (2021.01)

(52) U.S. Cl.
CPC .................................... *A61B 5/346* (2021.01)

(58) Field of Classification Search
CPC ......... A61B 5/318; A61B 5/319; A61B 5/327; A61B 5/346
See application file for complete search history.

(56) References Cited

U.S. PATENT DOCUMENTS

| | | | | |
|---|---|---|---|---|
| 2002/0035334 A1* | 3/2002 | Meij | ...................... | A61B 5/308 600/509 |
| 2021/0267525 A1* | 9/2021 | Albert | ...................... | A61B 5/28 |
| 2025/0111516 A1* | 4/2025 | Slomka | ...................... | G06T 7/11 |

OTHER PUBLICATIONS

Jose M. Sanchez, MD., "A Novel Approach to Electrocardiography in the Prone Patient", Article, 2020, 1-3, vol. 2, No. 1, Heart Rhythm O2.

Hugo Roccia, "Electrocardiogram Monitoring in the Prone Position in Coronavirus Disease 2012 Acute Respiratory Distress Syndrome", Report, 2021, 792-796, vol. 20, European Journal of Cardiovascular Nursing.

David Chieng, "Prone and Supine 12-Lead ECG Comparisons", Article, 2021, 1-10, vol. 7, No. 11, Clinical Electrophysiology.

* cited by examiner

*Primary Examiner* — Eric D. Bertram
(74) *Attorney, Agent, or Firm* — Hayes Soloway P.C.

(57) ABSTRACT

The present invention relates to a method for obtaining an electrocardiogram of a subject in a prone position, which comprises the steps of obtaining two leads (D1 and D2) from four electrodes positioned on the left arm (L), the right arm (R), the left leg (F), and the right leg (neutral electrode) of the subject selected from I, II, III, aVR, aVL, and aVF; obtaining a lead (DP) from one or more electrodes located on the back of the subject, as the potential difference between the additional electrode and a Wilson's central terminal (WCT); and obtaining precordial leads (V1 to V6), which define a derived ECG, from leads D1, D2, and DP.

8 Claims, 5 Drawing Sheets

METHOD FOR OBTAINING AN ELECTROCARDIOGRAM IN PRONATED SUBJECTS

CROSS-REFERENCE TO RELATED APPLICATIONS AND PRIORITY

This patent application claims priority from European Patent Application No. 23383226.0 filed Nov. 29, 2023.

OBJECT OF THE INVENTION

The object of the invention relates to a method for obtaining a conventional twelve-lead electrocardiogram (ECG) of subjects in a prone position, which allows reducing the number electrodes used in a standard ECG and preventing the need to place electrodes on the front of the chest.

BACKGROUND OF THE INVENTION

Conventional electrocardiogram (ECG) uses a series of electrodes placed on the limbs (four electrodes) and in the anterior region of the chest (six electrodes) to obtain twelve records of the electrical activity of the heart, known as leads, as shown in FIG. 1.

These twelve leads are essentially twelve spatially different perspectives of the electrical activity of the heart. Leads are divided into two groups: limb leads and precordial leads.

Limb leads record the potential differences between the electrodes placed on the arms and the legs. In particular, the electrode on the right leg is used to reduce different types of interference. In medical literature, it is called "neutral", "ground", or "reference" electrode.

Precordial leads (V1 to V6) are obtained from electrodes placed at specific points in the front of the chest. These leads measure the potential difference between these thoracic points and the Wilson's central terminal (WCT), which is formed by joining the limbs by means of cables and resistances as follows:

$$\text{Potential } WCT = (\text{Potential } R + \text{Potential } L + \text{Potential } F)/3$$

Therefore, ECG provides a three-dimensional image of the electrical activity of the heart, which allows physicians to diagnose different heart conditions, through these twelve leads.

The use of ten electrodes entails problems in many clinical situations, and various systems that reconstruct the twelve leads of the standard electrocardiogram from a reduced number of electrodes positioned at different points of the body surface have been developed to that end.

The most well-known is the EASI system which obtains the twelve leads of conventional electrocardiogram from signals of five electrodes located on the torso, as shown in FIG. 2, and is very widely used for the electrocardiographic monitoring of hospitalized patients.

Other reduced systems, such as the Holter system, have been used for ambulatory electrocardiography, also for recording cardiac activity while exercising, or for reconstructing noisy signals or signals with artifacts.

The prone position (patient facing down in bed) optimizes oxygenation in cases of severe respiratory failure. This position favors lung ventilation and perfusion, which can in turn improve respiratory function and reduce the need for invasive mechanical ventilation. In intubated patients, this position has been associated with better gas exchange and has improved prognosis.

The prone position is successfully used in patients with acute respiratory distress syndrome (ARDS) and has been widely used in patients with COVID-19.

Performing a conventional electrocardiogram in this position using the solutions of the state of the art is impossible because the anterior plane of the chest cannot be reached to place the precordial electrodes.

In practice, when there is a need to perform an ECG on a patient in a prone position, the patient is turned to a supine position, and the ECG is thereby obtained. This maneuver, called "de-proning" hereinafter, can be very complicated in patients with multiple lines and sensors. Alternatively, in these patients, electrocardiograms are performed by transposing the precordial electrodes to the back, as shown in FIG. 3. The precordial leads thus obtained shows a morphology that is very different from that of the conventional electrocardiogram and have reduced diagnostic value.

Therefore, there is a need to develop a method for obtaining conventional electrocardiograms using a reduced number of electrodes located at readily accessible points on a patient in a prone position.

DESCRIPTION OF THE INVENTION

The object of the present invention focuses on a method for obtaining a conventional ECG (electrocardiogram) with twelve leads (records of the electrical activity of the heart) of subjects in a prone position. The twelve leads of the conventional ECG are 6 standard limb leads (I, II, III, aVR, aVL, and aVF) and 6 precordial leads (V1 to V6).

The method of the invention comprises placing four electrodes on the limbs of the subject in a prone position such that their positions coincide with those of the electrodes placed in the ECGs of the state of the art, called standard ECGs, and at least an additional electrode located on the back of the subject. Specifically, the number of additional electrodes is less than 6.

The limbs of the subject in a prone position are the right leg, the left leg, the right arm, and the left arm.

Particularly, the method of the invention comprises a step of obtaining standard limb leads (I, II, III, aVR, aVL, and aVF) of the subject in a prone position from the four electrodes positioned on the limbs, particularly the left arm (L), the right arm (R), the left leg (F), and the right leg (neutral electrode).

Preferably, the step for obtaining standard limb leads is performed using the following relationships:

$$\text{Lead } I = \text{Potential } L - \text{Potential } R$$

$$\text{Lead } II = \text{Potential } F - \text{Potential } R$$

$$\text{Lead } III = \text{Potential } F - \text{Potential } L$$

$$\text{Lead } aVR = \text{Potential } R - 1/2(\text{Potential } L + \text{Potential } F)$$

$$\text{Lead } aVL = \text{Potential } L - 1/2(\text{Potential } F + \text{Potential } R)$$

$$\text{Lead } aVF = \text{Potential } F - 1/2(\text{Potential } L + \text{Potential } R)$$

The method of the invention further comprises a step of obtaining a posterior lead (DP) from at least an additional electrode positioned on the back of the subject, preferably on a left paravertebral line of the subject in a prone position at the level of the seventh/eighth thoracic vertebra (D7/D8) or on a midline of the back of the subject in a prone position at the level of vertebra D7, or at a distance of less than 5 cm from said vertebra D7. This posterior lead (DP) records the potential difference between the additional electrode and a Wilson's central terminal.

Wilson's central terminal (WCT), as explained, is formed by joining the limbs by means of cables and resistances as follows:

$$\text{Potential } WCT = (\text{Potential } R + \text{Potential } L + \text{Potential } F)/3$$

As explained, preferably, the one or more electrodes located on the back can be arranged on the left paravertebral line at the level of T7-T8, which is the position equivalent to the fifth intercostal space at the anterior level and corresponds with the lower end of the shoulder blade.

Placement of the rear electrode at a point precisely located with anatomical references is important as long as general formulas are used for the lead of the precordial leads. If methods for obtaining the precordial leads (second and third embodiments of the invention) in a customized manner are used, the exact position of the dorsal electrode is less decisive.

Next, the method of the invention comprises a step of processing the standard leads and the posterior lead (DP) to obtain precordial leads (V1 to V6) by means of formula:

$$V_n = A_n * D_1 + B_n * D_2 + C_n * DP$$

wherein D1 and D2 are two standard leads selected from leads I, II, III, aVR, aVL, and aVF, DP is the posterior lead, and An, Bn, and Cn are previously obtained coefficients.

Three different methods, which are explained below and which could be used in different clinical situations, can be used to obtain coefficients An, Bn, and Cn.

In a first embodiment of the invention, the coefficients used for obtaining the 6 precordial leads (V1 to V6) are a set of universal coefficients (A'n, B'n, and C'n). Universal coefficients (A'n, B'n, and C'n) are obtained by means of a theoretical computational model of the human chest, using electrocardiographic record databases, which include a sample series from "normal" subjects. Preferably, the computational model used includes a least squares regression to obtain the value of the universal coefficients.

In a preferred embodiment, leads I, II, and the posterior lead (DP) can be used such that the six precordial leads (V1 to V6) are obtained from the formula:

$$V_n = A'_n * I + B'_n * II + C'_n * DP$$

The defined formula allows each of the precordial leads ($V_n$) to be derived from the values of leads I and II and the posterior lead (DP) using universal coefficients ($A'_n$, $B'_n$, and $C'_n$).

In this case, the universal coefficient $A'_n$ can take the values of:

$$A'_1 = [-0.8; -0.52]$$

$$A'_2 = 0$$

$$A'_3 = [0.81; 1.2]$$

-continued $$A'_4 = [1; 1.7]$$

$$A'_5 = [1; 1.6]$$

$$A'_6 = [0.92; 1.2]$$

The universal coefficient $B'_n$ can take the values of:

$$B'_1 = [-0.13; 0.13]$$

$$B'_2 = 0$$

$$B'_3 = [0.23; 0.33]$$

$$B'_4 = [0.4; 0.45]$$

$$B'_5 = 0.5$$

$$B'_6 = [0.36; 0.48]$$

And the universal coefficient $C'_n$ can take the values of:

$$C'_1 = [-2.7; -1.9]$$

$$C'_2 = -4.3$$

$$C'_3 = [-4.1; -3.6]$$

$$C'_4 = [-2; -1.4]$$

$$C'_5 = [-0.37; -0.3]$$

$$C'_6 = 0.6$$

As explained above, precordial leads could also be obtained from the combination of a different pair of standard leads and posterior lead (DP).

The universal coefficients for the cases in which the standard leads are other than leads I and II, can preferably be obtained mathematically by means of relationships between standard leads III, aVR, aVL, and aVF and standard leads I and II, known in the state of the art. This approach is used in electrocardiogrameasuring leads I and II, and mathematically obtaining standard leads III, aVR, aVL, and aVF.

Obtaining precordial leads using universal coefficients assumes that the relationship between the electrical activity generator (the heart) and the body surface is identical in all the subjects. This is a simplification, such that the method of the invention can obtain the coefficients ($A_n$, $B_n$, and $C_n$) as particularized coefficients ($A''_n$, $B''_n$, and $C''_n$), typical of each subject.

In this second embodiment of the invention, a standard ECG, i.e., with 12 electrodes placed in conventional positions, of a subject performed in a supine position, is used.

A derived ECG is furthermore determined depending on the value of the particularized coefficients (A"n, B"n, and C"n) of the subject.

The particularized coefficients (A"n, B"n, and C"n) of the subject are obtained from the standard ECG of the patient and from the electrocardiographic record of the limb leads and of the posterior lead, using a computational model, as those that minimize the difference between the original standard ECG and the derived ECG, obtained with the formula:

$$Vn = A''n * D1 + B''n * D2 + C''n * DP.$$

The particularized coefficients (A"n, B"n, and C"n) are typical of each subject, and therefore every time a new electrocardiographic record of the patient in a prone position is obtained, a derived ECG with a small error rate with respect to the standard ECG of the subject can be obtained. Preferably, the computational model used is a least squares linear regression. Alternatively, other computational models such as non-linear optimization models or independent component analysis, among others, can be used. In general, these techniques prioritize the similarity of parts having a higher voltage of the ECG (QRS complex), "sacrificing" elements having a lower voltage (P wave, ST segment, T wave). For this reason, algorithms which fragment the ECG signal and obtain different coefficients for different fragments of the signal: P wave, QRS, ST, T wave, have also been proposed.

In a third embodiment of the invention, the coefficients (An, Bn, and Cn) can be obtained as particularized artificial intelligence coefficients (A'"n, B'"n, and C'"n), which would also provide an individualized synthesis for each subject.

In this case, to obtain the 12 leads of the conventional electrocardiogram, a machine learning system trained with the standard ECG of the subject that would then generate a derived ECG from leads I, II, and DP of the subject, could be used. In particular, algorithms of the time delay neural network or bidirectional long-short memory type can be used.

With any of the computational methods, the method of the invention enables obtaining a conventional electrocardiogram for the continuous monitoring of the cardiac situation of a subject in a prone position, thereby solving the current problem of not being possible to perform electrocardiograms with full diagnostic capability on subjects who are in this position.

DESCRIPTION OF THE DRAWINGS

To complement the description that is being made and for the purpose of helping to better understand the features of the invention according to a preferred practical exemplary embodiment thereof, a set of drawings is attached as an integral part of said description in which the following is depicted in an illustrative and non-limiting manner.

PREFERRED EMBODIMENT OF THE INVENTION

A preferred embodiment of the method for obtaining an electrocardiogram of subjects in a prone position is described below with the help of FIGS. 1 to 7.

Figure 1:
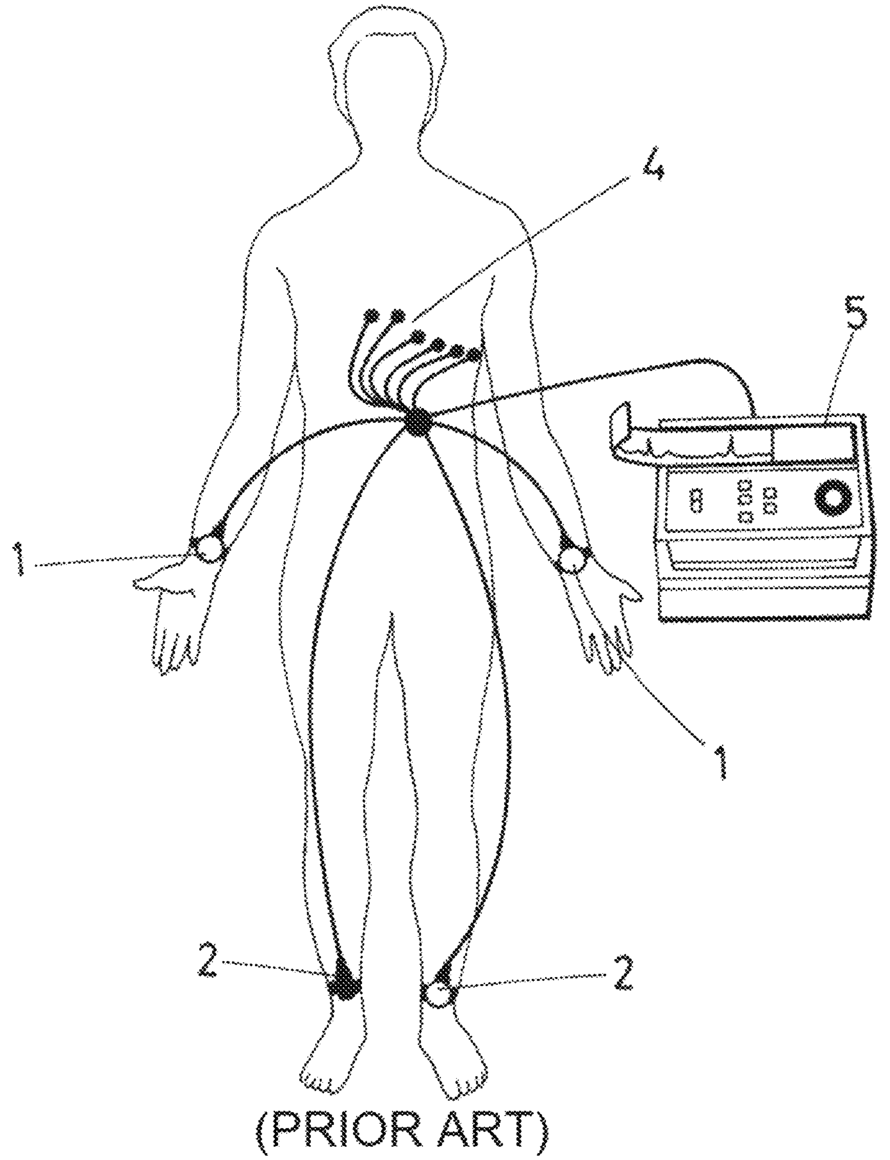
(PRIOR ART) FIG.1
FIG. 1 shows a depiction of an electrocardiogram of the state of the art, with ten electrodes, arranged on the torso and the limbs of a subject.
Figure 2:
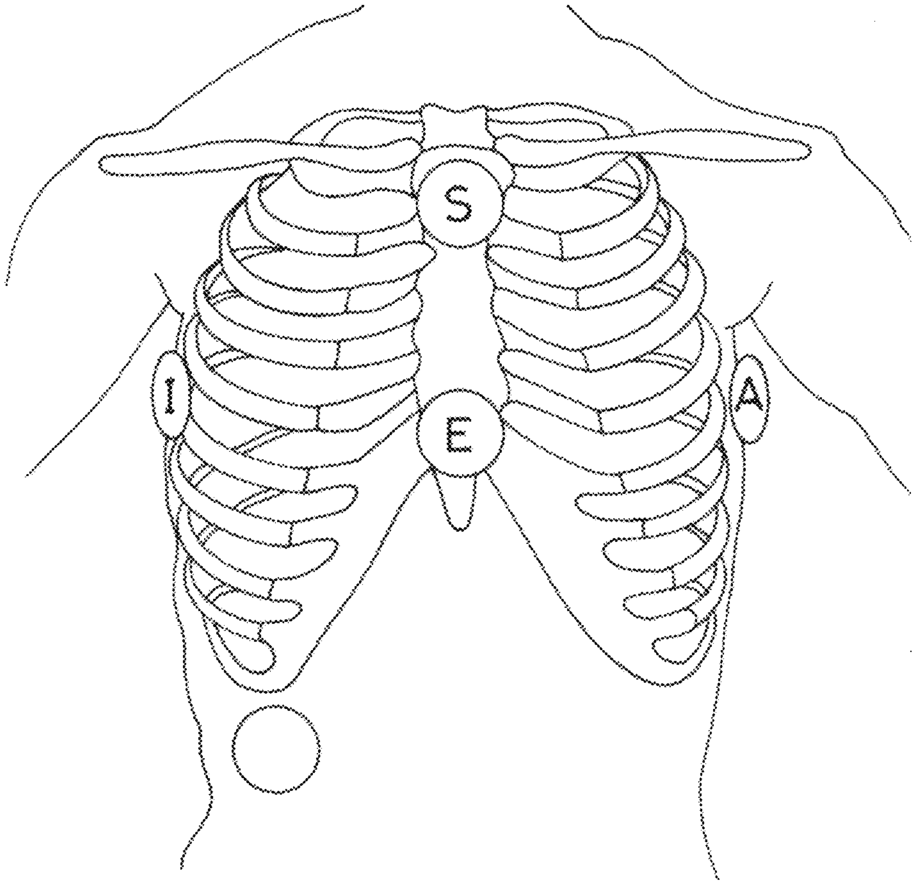
(PRIOR ART) FIG.2
FIG. 2 shows the position of the electrodes in the EASI system.

FIG. 1 shows a depiction of a patient or subject on whom an electrocardiogram of the state of the art is being performed. In electrocardiograms of this type, two upper limb electrodes (1) are located on the arms, two lower limb electrodes (2) are located on the legs, and six electrodes (4) are distributed in anatomically defined locations of the anterior area of the chest. All the electrodes (1, 2, 4) are connected to a processor (5).

As can be seen in this figure, the wiring is complex and the electrocardiogram cannot be performed on a subject who is in a prone position.

Figure 3:
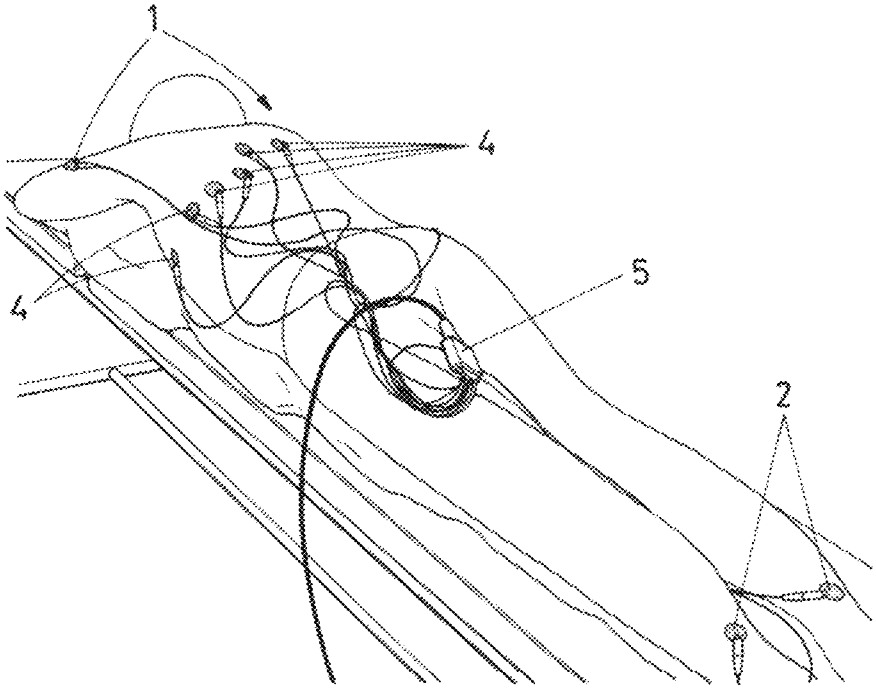
(PRIOR ART) FIG. 3
FIG. 3 shows the way in which electrocardiograms are currently performed on subjects in a prone position. The ECG thus obtained has limited diagnostic capability.
Figure 4:
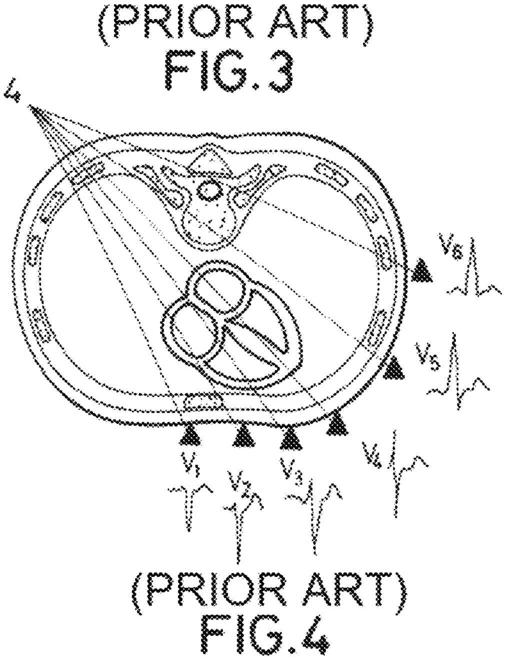
(PRIOR ART) FIG. 4
FIG. 4 shows a schematic depiction of a section of the torso of a subject in which the thoracic electrodes of an electrocardiogram of the state of the art are shown arranged in the front of the torso to perform a conventional electrocardiogram.

Therefore, at present, when an electrocardiogram is to be performed on a patient in a prone position, the precordial leads are transposed to the back of the subject as shown in FIG. 3. In this case, the upper limb electrodes (1), the lower limb electrodes (2), and the six electrodes (4), distributed in this case in the lower part of the torso, are also used.

The electrocardiograms performed using this method have limited diagnostic value.

However, as shown in FIG. 3, performing a traditional electrocardiogram with six electrodes (4) on the back is still extremely complex and unpleasant, both for the patient and for the specialist, due to the large number of electrodes to be placed, as well as to all the wiring associated therewith. Furthermore, the ECG thus obtained is morphologically different from the standard ECG obtained in a supine position, so it has little diagnostic value.

For this reason, the method for obtaining electrocardiograms of the present invention greatly facilitates the work of health personnel, and it is also extremely beneficial for patients suffering from pathologies of this type, since the electrocardiogram can be performed with the patient being in a prone position, and using a single electrode (3) on the back. More importantly, it allows obtaining an ECG in a prone position similar to the standard ECG obtained in a supine position, causing it to have a high diagnostic value.

Figure 5:
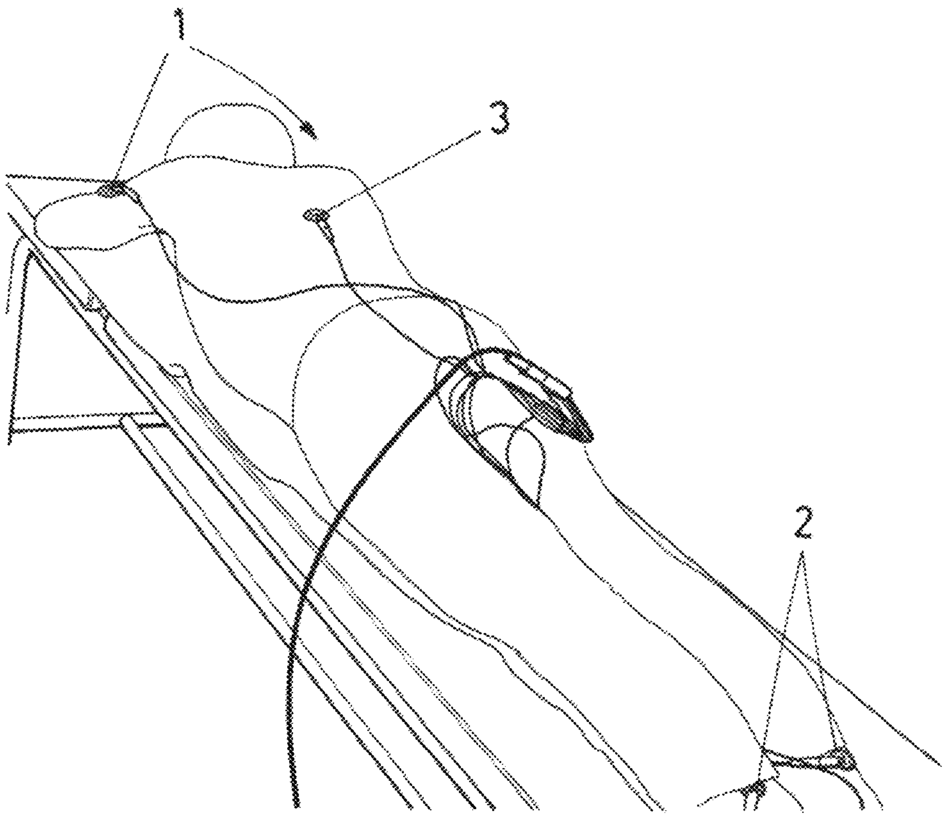
FIG. 5 shows a depiction of the arrangement of the electrodes of the electrocardiogram of the present invention with an electrode positioned on the back and the other four electrodes on the limbs.
Figure 6:
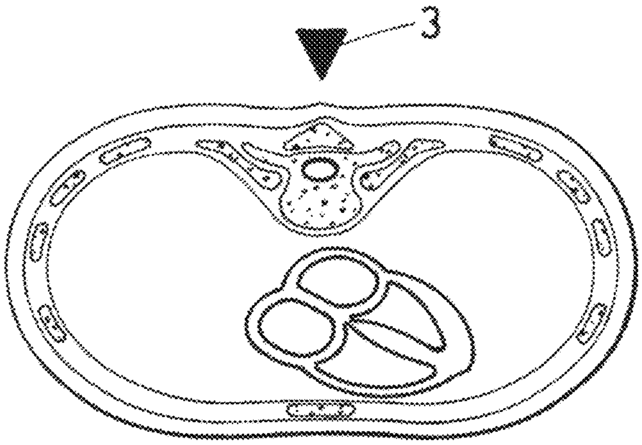
FIG. 6 shows a schematic depiction of a section of the torso of a subject in which the electrode positioned on the back is reflected in an electrocardiogram of the method of the present invention.

Particularly, FIGS. 5 and 6 show a depiction of the arrangement of the electrodes to perform the method of the invention, which comprises the following steps:

- Obtaining conventional limb leads (I, II and III, aVR aVL and aVF) with the electrodes (1, 2) positioned on arms and legs like in a standard ECG,
- Obtaining a lead DP from at least one electrode (3) located on the back of the subject, and
- Sending leads I, II, and DP to a processor (5) to obtain the precordial leads (V1 to V6), applying the formula:

$$V_n = A_n * I + B_n * II + C_n * DP$$

with the coefficients $A_n$, $B_n$ and $C_n$ being comprised in a range of ±10% of the following values:

| | I $A_n$ | II $B_n$ | DP $C_n$ |
|---|---|---|---|
| V1 | −0.8 | 0.13 | −2.7 |
| V2 | 0 | 0 | −4.3 |
| V3 | 1.2 | 0.23 | −4.1 |
| V4 | 1.7 | 0.4 | −2 |
| V5 | 1.6 | 0.5 | −0.37 |
| V6 | 1.2 | 0.36 | 0.6 |

The coefficients A, B, and C are different for each of the precordial leads $V_n$ and are based on the reconstruction of the electrocardiogram using a reference vector system from a set of leads which is not used up until now, and because they are different from those used previously in other simplified electrocardiograms.

Alternatively, the construction of the final electrocardiographic signal can be performed individually, generating a set of specific coefficients for each patient using conventional computing techniques or machine learning methods.

In one aspect of the invention, the lead DP is obtained from a single electrode (3) located on the back of the subject, particularly close to the midline of the back of the subject.

Alternatively, it could be obtained from several electrodes (3) placed on the back of the patient close to the midline.

In different alternative aspects of the invention, electrode or electrodes (3) used to obtain the lead DP can be placed:

on a midline of the back of the subject in a prone position at the level of vertebra D7, which is the position equivalent to the fifth intercostal space at the anterior level and corresponds with the lower end of the shoulder blade, or on the left paravertebral line at the level of the seventh/eighth thoracic vertebra (D7/D8).

Figure 7:
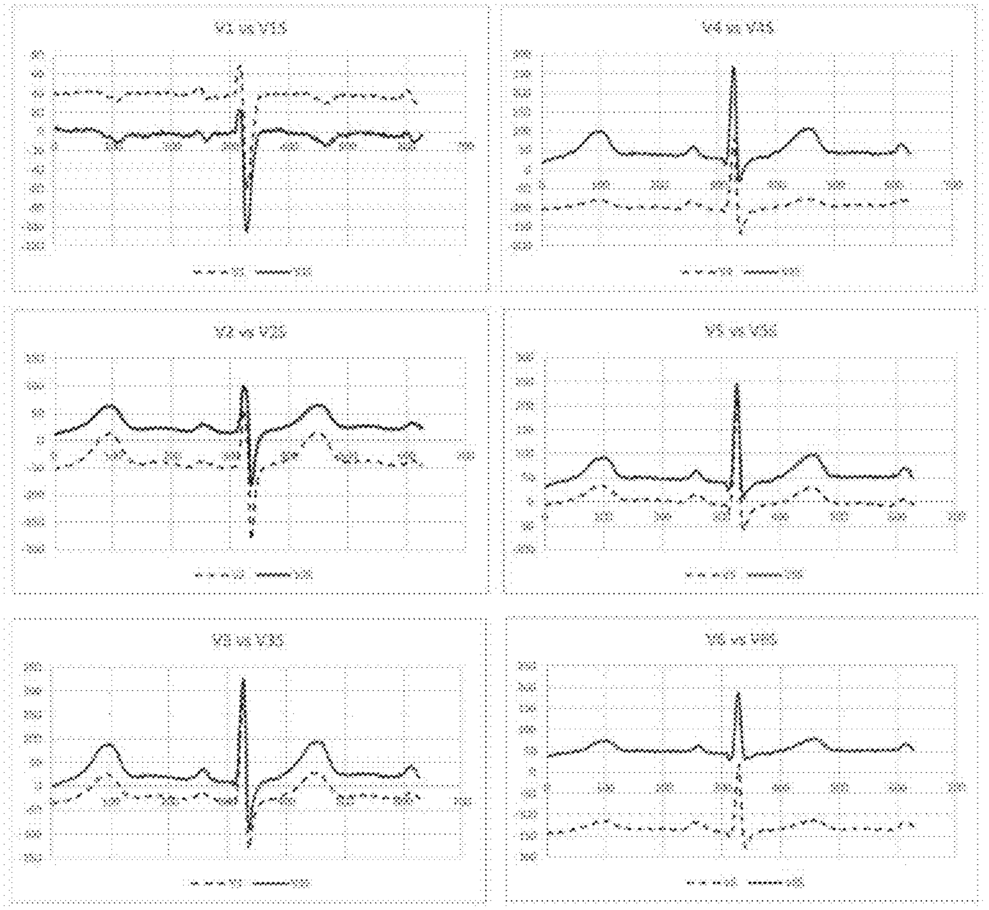
FIG. 7 shows a comparison of the leads obtained from a subject in a prone position with the method of the invention ($V_n$S) compared to those recorded in the same subject in a supine position with the standard method, with the electrodes being arranged in the anterior thorax (Vn).

Lastly, and for the purpose of showing the validity of the method, FIG. 7 shows graphs of the precordial leads obtained for a patient particularly with the method of the invention $V_n$S in comparison to those recorded in the same patient with the standard method, with the electrodes (3) arranged in the anterior thorax (Vn).

As can be seen, the signals of each precordial lead and the synthesized counterpart thereof are practically identical.

The invention claimed is:

1. A method for obtaining an electrocardiogram of a subject in a prone position, which comprises the steps of:

obtaining a first lead and a second lead from four electrodes positioned on the left arm, the right arm, the left leg, and the right leg of the subject selected from:

$$I = \text{Potential-}L - \text{Potential } R$$

$$II = \text{Potential-}F - \text{Potential } R$$

$$III = \text{Potential-}F - \text{Potential } L$$

$$aVR = \text{Potential } R - 1/2(\text{Potential } L + \text{Potential } F)$$

$$aVL = \text{Potential } L - 1/2(\text{Potential } F + \text{Potential } R)$$

$$aVF = \text{Potential } F - 1/2(\text{Potential } L + \text{Potential } R).$$

wherein I, II, III, aVR, aVL, and aVF are standard limb leads; L refers to potential measured on the left arm, R refers to potential measured on the right arm, F refers to the potential measured on left leg, and the electrode on the right leg is configured as a neutral electrode, obtaining a third lead from one or more electrodes located on the back of the subject, representing the potential difference between said electrodes and a Wilson's central terminal (WCT);

obtaining six precordial leads, which define a derived ECG, from the first lead, the second lead and the third lead by:

applying the formula:

$$V_n = A'_n * D1 + B'_n * D2 + C'_n * DP$$

wherein D1 and D2 refer to the first lead and the second lead, DP refers to the third lead, and the coefficients $A'_n$, $B'_n$, and $C'_n$ are obtained by a theoretical computational model of the human chest, using electrocardiographic record databases, which include a sample series from normal subjects;

applying the formula:

$$V_n = A''_n * D1 + B''_n * D2 + C''_n * DP$$

wherein the coefficients $A''_n$, $B''_n$, and $C''_n$ are obtained by: obtaining a standard ECG of 12 electrodes placed on the subject in a supine position and applying a computational model which determines the coefficients as those that minimize the difference between the derived ECG and the standard ECG; or obtaining a standard ECG of 12 electrodes placed on a patient in a supine position and applying a machine learning system trained with the standard ECG of the patient and the first lead, the second lead, and the third lead of the patient.

2. The method according to claim 1, wherein the computational model which determines the coefficients $A''_n$, $B''_n$, and $C''_n$ is a least squares linear regression.

3. The method according to claim 1, wherein the computational model which determines the coefficients $A''_n$, $B''_n$, and $C''_n$ is selected from non-linear optimization models or independent component analysis models.

4. The method according to claim 1, wherein the third lead is obtained from one or more electrodes-located on a left paravertebral line of the subject in a prone position at the level of the seventh/eighth thoracic vertebra or on a midline of the back of the subject in a prone position at the level of the seventh thoracic vertebra.

5. The method according to claim 4, wherein the third lead is obtained from a single electrode located on the left paravertebral line of the subject in a prone position at the level of the seventh/eighth thoracic vertebra or on the midline of the back of the subject in a prone position at the level of the seventh thoracic vertebra.

6. The method according to claim 1, wherein the first lead and the second lead correspond to leads I and II, and wherein the universal coefficients $A'_n$, $B'_n$, and $C'_n$ take the values of:

$$A'_1 = [-0.8; -0.52]$$

$$A'_2 = 0$$

-continued $A'_3 = [0.81; 1.2]$ $A'_4 = [1; 1.7]$ $A'_5 = [1; 1.6]$ $A'_6 = [0.92; 1.2]$ $B'_1 = [-0.13; 0.13]$ $B'_2 = 0$ $B'_3 = [0.23; 0.33]$ $B'_4 = [0.4; 0.45]$ $B'_5 = 0.5$ $B'_6 = [0.36; 0.48]$ $C'_1 = [-2.7; -1.9]$ $C'_2 = -4.3$ -continued $C'_3 = [-4.1; -3.6]$ $C'_4 = [-2; -1.4]$ $C'_5 = [-0.37; -0.3]$ $C'_6 = 0.6.$

7. The method according to claim 1, wherein the universal coefficients $A'_{n1}$, $B'_{n1}$, and $C'_{n1}$ for a specific combination of the first lead and the second lead are obtained from the values of the universal coefficients $A'_{n2}$, $B'_{n2}$, and $C'_{n2}$ for another combination of the first lead and the second lead by relationships between the leads.

8. The method according to claim 1, wherein the trained machine learning system uses algorithms selected from: time delay neural network or bidirectional long-short memory.

* * * * *